(12) United States Patent
Chao et al.

(10) Patent No.: US 10,806,403 B2
(45) Date of Patent: Oct. 20, 2020

(54) ADAPTIVE CONTROLLER USED IN PHOTOPLETHYSMOGRAPHY SENSING SYSTEM

(71) Applicant: National Chiao Tung University, Hsinchu (TW)

(72) Inventors: Paul C. P. Chao, Taipei (TW); Tse-Yi Tu, Taipei (TW); Bo-Wei Pan, Taoyuan (TW); Yan-Hwa Wu, Hsinchu (TW)

(73) Assignee: National Chiao Tung University, Hsinchu (TW)

( * ) Notice: Subject to any disclaimer, the term of this patent is extended or adjusted under 35 U.S.C. 154(b) by 364 days.

(21) Appl. No.: 15/648,989

(22) Filed: Jul. 13, 2017

(65) Prior Publication Data

US 2018/0317854 A1 Nov. 8, 2018

(30) Foreign Application Priority Data

May 8, 2017 (TW) .............................. 106115201 A

(51) Int. Cl.
| | |
|---|---|
| *A61B 5/00* | (2006.01) |
| *A61B 5/021* | (2006.01) |
| *A61B 5/024* | (2006.01) |
| *A61B 5/026* | (2006.01) |
| *A61B 5/145* | (2006.01) |
| *A61B 5/1455* | (2006.01) |

(52) U.S. Cl.
CPC .......... *A61B 5/7225* (2013.01); *A61B 5/0059* (2013.01); *A61B 5/021* (2013.01); *A61B 5/0261* (2013.01); *A61B 5/02416* (2013.01); *A61B 5/14532* (2013.01); *A61B 5/14551* (2013.01); *A61B 5/7221* (2013.01)

(58) Field of Classification Search
CPC ....... A61B 5/72; A61B 5/7203; A61B 5/7221; A61B 5/7225; A61B 5/0059; A61B 5/02416; A61B 5/021
See application file for complete search history.

(56) References Cited

U.S. PATENT DOCUMENTS

| 10,244,987 B2 | 4/2019 | Chong et al. | |
| 2017/0042484 A1* | 2/2017 | Chong ................. | A61B 5/1455 |

FOREIGN PATENT DOCUMENTS

TW 201705900 A 2/2017

OTHER PUBLICATIONS

Office Action of corresponding TW application, published on Apr. 27, 2018.

* cited by examiner

*Primary Examiner* — Carolyn A Pehlke
(74) *Attorney, Agent, or Firm* — Wang Law Firm, Inc.

(57) ABSTRACT

An adaptive controller used in a photoplethysmography sensing system, comprises a plurality of hardware circuits which are configured to: receive a photoplethysmography signal (hereinafter, "PPG signal") processed; determine whether the PPG signal processed satisfies with a requirement; output the PPG signal processed if the PPG signal processed satisfies with a requirement; and adjust a gain of an amplifier for amplifying the PPG signal and/or a driving signal of a light source if the PPG signal processed does not satisfy with a requirement.

6 Claims, 8 Drawing Sheets

ADAPTIVE CONTROLLER USED IN PHOTOPLETHYSMOGRAPHY SENSING SYSTEM

CROSS-REFERENCE TO RELATED APPLICATION

This application claims priority from Taiwan Application No. 106115201, filed on May 8, 2017, in the Taiwan Intellectual Property Office, the content of which is hereby incorporated by reference in their entirety for all purposes.

BACKGROUND OF THE INVENTION

1. Field of the Invention

The present disclosure relates to a photoplethysmography sensing system, in particular, to a photoplethysmography sensing system using ad adaptive controller therein.

2. Description of the Related Art

Photoplethysmography can be used to acquire physiology information of a living object, such as heart rate, pulse, blood pressure and son on. Concept of photoplethysmography is illustrated as follows. When a beam emits to a skin surface of the living object, the beam is affected by blood flow variation to have variation. Specifically, when blood volume in blood vessels is relatively large, energy of the beam is absorbed relatively much. Thus, photoplethysmography is used to receive the reflection beam which the beam is reflected from the skin surface of the living object to obtain a photoplethysmography signal (PPG signal), and acquire the physiology information of the living object.

Since amplitude of the PPG signal is not large, a conventional photoplethysmography sensing system usually amplifies the PPG signal with a constant gain firstly, and then processes and analyzes an amplified PPG signal. In addition, the conventional photoplethysmography sensing system keeps amplitude of a driving signal (i.e. driving current or voltage) of a light source constant, so as to provide a beam with constant intensity emitting to the skin surface of the living object.

However, the PPG signal is affected by a skin color, a skin thickness, a measuring position and a blood vessel thickness easily. Thus, amplifying the PPG signal with the constant gain cannot obtain the PPG signal with good signal quality. In addition, if the conventional photoplethysmography sensing system configures the light source emits the beam with a maximum power, problems of signal saturation and power waste may occur for some users.

Furthermore, when the conventional photoplethysmography sensing system obtains the PPG signal, whether a photo sensor receives a reflection beam which the beam generated by the light source is reflected from the skin surface is determined according to the amplitude of the PPG signal. Thus, if the PPG signal is amplified with the constant gain and the amplitude of the amplified PPG signal is still small, the user should adjust the measuring position, so as to find the optimal measuring position for obtaining the PPG signal with the sufficiently large amplitude. Or alternatively, regardless of increasing cost, the manufacturer of the conventional photoplethysmography sensing system can use a light source array and a photo sensor array to implement the conventional photoplethysmography sensing system, so as to prevent from receiving the PPG signal with the small amplitude.

Moreover, if the amplitude of PPG signal cannot falls within an optimal processing range of digital processing (for example, when the PPG signal is dedicated to acquire the blood pressure, the PPG signal should be digitally processed), the corresponding physiology information cannot acquired successfully. For example, if the amplitude of the PPG signal is too large to fall out the processing range of digital processing, the conventional photoplethysmography sensing system cannot further find the time point of the peak of the PPG signal, and thus it results that the calculated pulse is not correct, and the calculated blood pressure is also not correct. By contrast, if the amplitude of the PPG signal is too small, the time point of the peak of the PPG signal found by the conventional photoplethysmography sensing system may be not correct, and thus it results that the error of the calculated pulse is large, and the calculated blood pressure is also not precise. In short, the problems that the acquired physiology information varying in time is not precise will occur when the amplitude of the PPG signal is too large or too small.

In other one aspect, amplitude of the driving signal of the light source in the conventional photoplethysmography sensing system cannot adjusted automatically, and thus when distortion introduces in the PPG signal, a driving circuit should be modified to adjust the amplitude of the driving signal to make the PPG signal have the better signal quality. Accordingly, this situation results inconvenience and trouble for the users.

SUMMARY OF THE INVENTION

To solve at least one of the above technical problems, one object of the present disclosure is to provide an adaptive controller used in a photoplethysmography sensing system, wherein the adaptive controller can adaptively adjust a gain of an amplifier and/or amplitude of a driving signal of a light source according to whether a processed PPG signal satisfies with a requirement, so as to obtain the PPG signal which has good signal quality or satisfies with the requirement, and increase measuring precision, stability and sensitivity.

According to at least one object of the present disclosure, an adaptive controller used in a photoplethysmography sensing system is provided, and comprises hardware circuits configured to: receive a processed PPG signal; determine whether the processed PPG signal satisfies with a requirement; output the processed PPG signal if the processed PPG signal satisfies with the requirement; and adjust a gain of an amplifier for amplifying a PPG signal and/or a driving signal of a light source if the processed PPG signal does not satisfy with the requirement.

According to at least one object of the present disclosure, a photoplethysmography sensing system is provided, and the photoplethysmography sensing system comprises above adaptive controller, light source and photo sensor.

Accordingly, the provided adaptive controller and photoplethysmography sensing system have benefits as follows.

(1) The adaptive controller makes the processed PPG signal have high stability, precision and sensitivity.

(2) The implementation cost of the adaptive controller is not high, the adaptive controller can be integrated in the photoplethysmography sensing system easily, and thus the present disclosure has low price advantage and light, thin, short and small properties.

(3) Since the processed PPG signal is optimized without user operation, and thus the photoplethysmography sensing system with the adaptive controller has advantage of simple and convenient operation.

DESCRIPTION OF THE EXEMPLARY EMBODIMENTS

The accompanying drawings are included to provide a further understanding of the present disclosure, and are incorporated in and constitute a part of this specification. The drawings illustrate exemplary embodiments of the present disclosure and, together with the description, serve to explain the principles of the present disclosure.

Although the terms "first," "second," etc. may be used herein to describe various elements, components, regions, layers, and/or sections, these elements, components, regions, layers, and/or sections should not be limited by these terms. These terms are used to distinguish one element, component, region, layer, and/or section from another element, component, region, layer, and/or section. Thus, a first element, component, region, layer, and/or section discussed below could be termed a second element, component, region, layer, and/or section without departing from the teachings of the present disclosure.

An exemplary embodiment of the present disclosure provides an adaptive controller used in a photoplethysmography sensing system, and the adaptive controller can adaptively adjust a gain of an amplifier and/or amplitude of a driving signal (driving current or voltage) of a light source according to whether a processed PPG signal satisfies with a requirement. Thus, the photoplethysmography sensing system can obtain the PPG signal which has increased signal quality, and the measuring precision, stability and sensitivity are thus enhanced. In addition, in another one exemplary embodiment, the algorithm for adaptively the gain of an amplifier and/or the amplitude of the driving signal of the light source can be artificial intelligence algorithm, so as to make the processed PPG signal satisfies with the requirement quickly.

Figure 1:
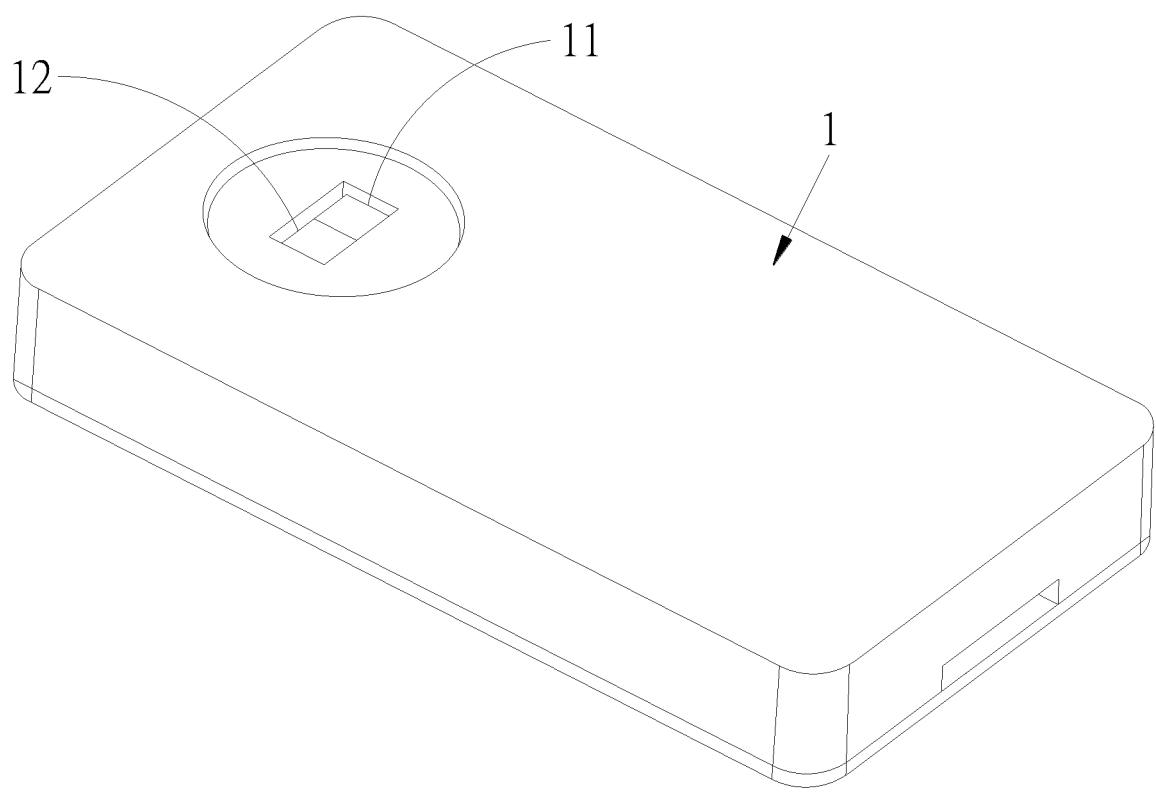
FIG. 1 is a schematic diagram of a photoplethysmography sensing system according to an exemplary embodiment of the present disclosure.

Referring to FIG. 1, FIG. 1 is a schematic diagram of a photoplethysmography sensing system according to an exemplary embodiment of the present disclosure. The photoplethysmography sensing system 1 in FIG. is a portable physiology information sensor. When operating the portable physiology information sensor, the portable physiology information sensor should be approximate to a skin surface of a living object. The portable physiology information sensor can acquire physiology information of heart rate, pulse, blood pressure, blood oxygen, blood flow and glucose through a PPG signal, and thus the portable physiology information sensor can be at least one of portable optical blood pressure meter, pulse and blood oxygen meter, non-invasive blood flow meter and non-invasive blood glucose meter. By the way, the above portable physiology information sensor can be designed to a wearable device, and the present disclosure does not limit the applications of the photoplethysmography sensing system 1.

In addition, the portable physiology information sensor can transmit a measured PPG signal and/or physiology information to an electronic device with communication ability, and the electronic device can display the PPG signal and/or physiology information; or alternatively, the measured PPG signal and/or physiology information can be transmitted to a cloud server to establish a physiology information database of the user, such that the purpose of managing and analyzing the physiology state of the user can achieved.

The photoplethysmography sensing system 1 comprises a light source 11 and a photo sensor 12. The light source 11 can be a light-emission diode (LED) or of other type of a light source, for example, a variable wavelength laser diode, and the present disclosure is not limited thereto. In addition, a number of the light source 11 can be larger than or equal to one, for example, multiple light sources 11 with same or different wavelengths. The light source 11 generates a beam emitting to the skin surface of the living object, and for example, there is radial artery, ulnar artery, brachial artery or microvessel underneath the skin surface.

The skin surface of the living object reflects the beam emitted from the light source 11 to generate a reflection beam, and the photo sensor 12 receives the reflection beam and converts the reflection beam into a PPG signal. Since the vessel pulse, blood composition and concentration variation underneath the skin surface affect absorbing rate of the beam, the reflection beam generated by the skin surface conveys the physiology information. The photoplethysmography sensing system 1 thus further comprises a rear-end circuit (not shown in FIG. 1, such as amplifier, calculation circuit, and communication circuit, and the present disclosure is not limited thereto) for amplifying and processing the PPG signal. In addition, the photo sensor 12 can be a general photodiode or other type of photoelectric conversion device, and the present disclosure is not limited thereto.

However, since variation exists in skin thicknesses, colors, vessel positions, genders, ages, races, blood compositions, diseases of different living objects as well as the variation of users' operations, the PPG signal may have poor signal quality if a constant gain is used to amplify the PPG signal generated by the photo sensor 12 through the reception of the reflection beam. Thus, the acquired physiology information is not correct. To solve the problems, the photoplethysmography sensing system 1 further comprises an adaptive controller (not shown in FIG. 1, comprising a peak detection circuit 53 and an error amplifier EAMP in FIG. 5 for example, and the present disclosure is not limited thereto). The adaptive controller can adjust the amplitude of the driving signal of the light source 11 (i.e. adjust the intensity of the beam emitted by the light source 11) or a gain of the amplifier according to whether the PPG signal being processed (such as amplified or filtered) satisfies with the requirement. Accordingly, under the case of the low cost, low power consumption and convenient measure operation, the photoplethysmography sensing system 1 can still obtain the good PPG signal.

There are multiple implementations of the adaptive controller in the exemplary embodiments of the present disclosure, and one is to implement by merely hardware circuits, and other one is to implement by incorporation of software and hardware circuits. In short, the present disclosure does not limit the implementation of the adaptive controller and the control method executed by the adaptive controller.

The adaptive controller in the exemplary embodiment of the present disclosure has small volume, and can be implemented easily and directly integrated into the photoplethysmography sensing system 1, and thus dimension and cost of the portable physiology information sensor of the preset disclosure are approximate to those the marketed photosensing physiology information sensor. In another one aspect, when the PPG signal being processed has poor signal quality or does not satisfy the requirement, the adaptive controller automatically adjust amplitude of the driving signal of the light source 11 and/or the gain of the amplifier without additional user's manual operation. Thus, the photoplethysmography sensing system 1 brings the convenience to the user, and precision, stability and sensitivity of the measured physiology information are enhanced.

In short, the adaptive controller or the control method executed in the adaptive controller according to exemplary embodiments of the present disclosure can solve the problems which the correct physiology information cannot be measured easily due to the PPG signal with the poor signal quality, and also solve the problem that the PPG signal is not correct since the photo sensor 12 is affected by the operation environment (such as the environment light or shocking of the living object) easily.

Figure 2:
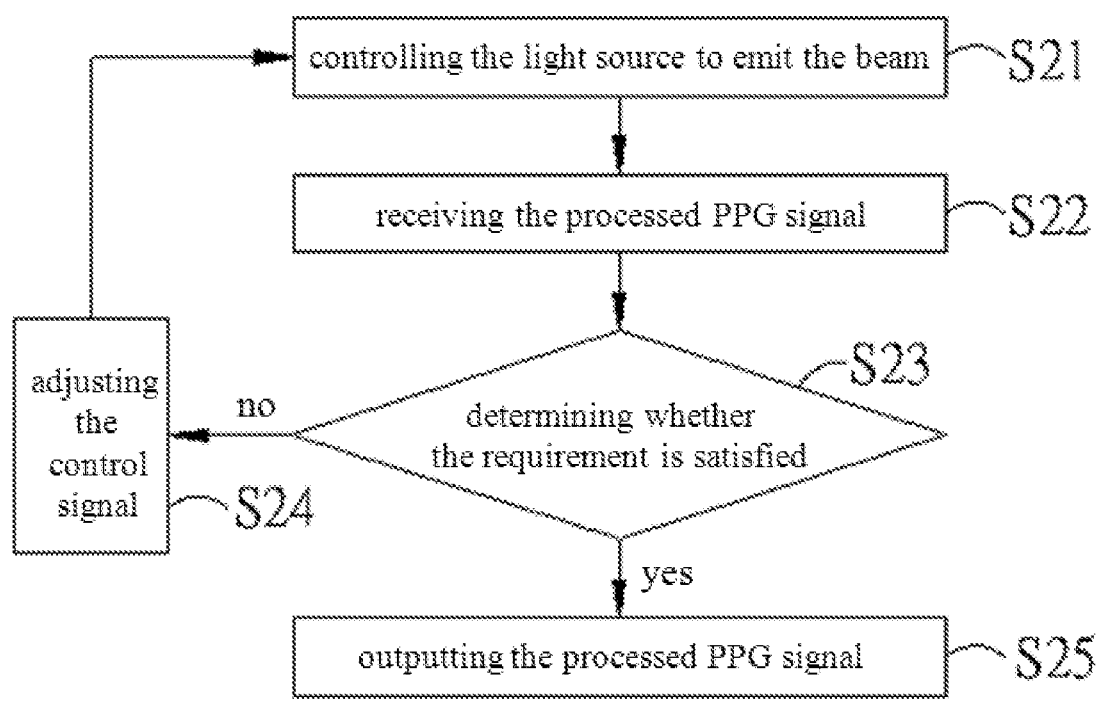
FIG. 2 is flow chart of a control method executed by an adaptive controller in a photoplethysmography sensing system according to an exemplary embodiment of the present disclosure.

Next, referring to FIG. 2, FIG. 2 is flow chart of a control method executed by an adaptive controller in a photoplethysmography sensing system according to an exemplary embodiment of the present disclosure. Firstly, at step S21, the adaptive controller is used to control the light source (for example, LED) to emit the beam to the skin surface of the living object according a control signal, wherein the intensity of the beam is determined according to the amplitude of the driving signal, and the driving signal is determined according to the control signal. Next, at step S22, the adaptive controller receives the processed PPG signal, wherein the skin surface of the living object reflects the beam emitted from the light source, and the photo sensor receives the reflection beam of the skin surface of the living object, and converts the reflection beam into the PPG signal. Next, at step S23, the adaptive controller determined whether the processed PPG signal satisfies with the requirement. If the processed PPG signal does not satisfy with the requirement, at step S24, the adaptive controller adjust the control signal which is used to determine the driving signal of the light source (i.e. adjust the intensity of the beam emitted by the light source at step S21), and then steps S21 through S23 are executed again. If the processed PPG signal satisfies with the requirement, at step S25, the adaptive controller outputs the received PPG signal to the circuit of the next stage. Steps S21 through S24 are executed repeatedly until the processed PPG signal satisfies with the requirement.

Process of at one of filtering and peak detection is performed on the PPG signal generated by the photo sensor to form the processed PPG signal at step S23, and the present disclosure does not limit the type of process. In addition, whether the processed PPG signal satisfies with the requirement is determined by whether the amplitude of and/or the signal stability of the processed PPG signal satisfies with the requirement. For example, whether the second peak of the processed PPG signal is found successfully is used to determine whether the processed PPG signal satisfies with the requirement. If the second peak of the processed PPG signal is found successfully, the intensity of the beam emitted by the light source should not be adjusted; if the second peak of the processed PPG signal is not found successfully, the intensity of the beam emitted by the light source should be adjusted, for example, the control signal is changed to adjust the amplitude of the driving signal of the light source.

For example, if the amplitude of the PPG signal generated by the photo sensor is too little, the processed PPG signal may have small amplitude and even distortion, and thus the sequent digital processing (comprising analog-to-digital conversion and numeric calculation) introduces relatively large error. By contrast, if the amplitude of the PPG signal generated by the photo sensor is too large, not only the problem of power waste exists, but also the problem that the amplitude of the processed PPG signal exceeds acceptable maximum value of the digital processing occurs. However, through the judging of step S23 and the adjusting of the control signal at step S24, at step S21, the intensity of the beam emitted by the light source can be adjusted, such that amplitude of the PPG signal generated by the photo sensor (or the processed PPG signal) falls within the predetermined threshold range, and the above problems can be avoided.

Figure 3:
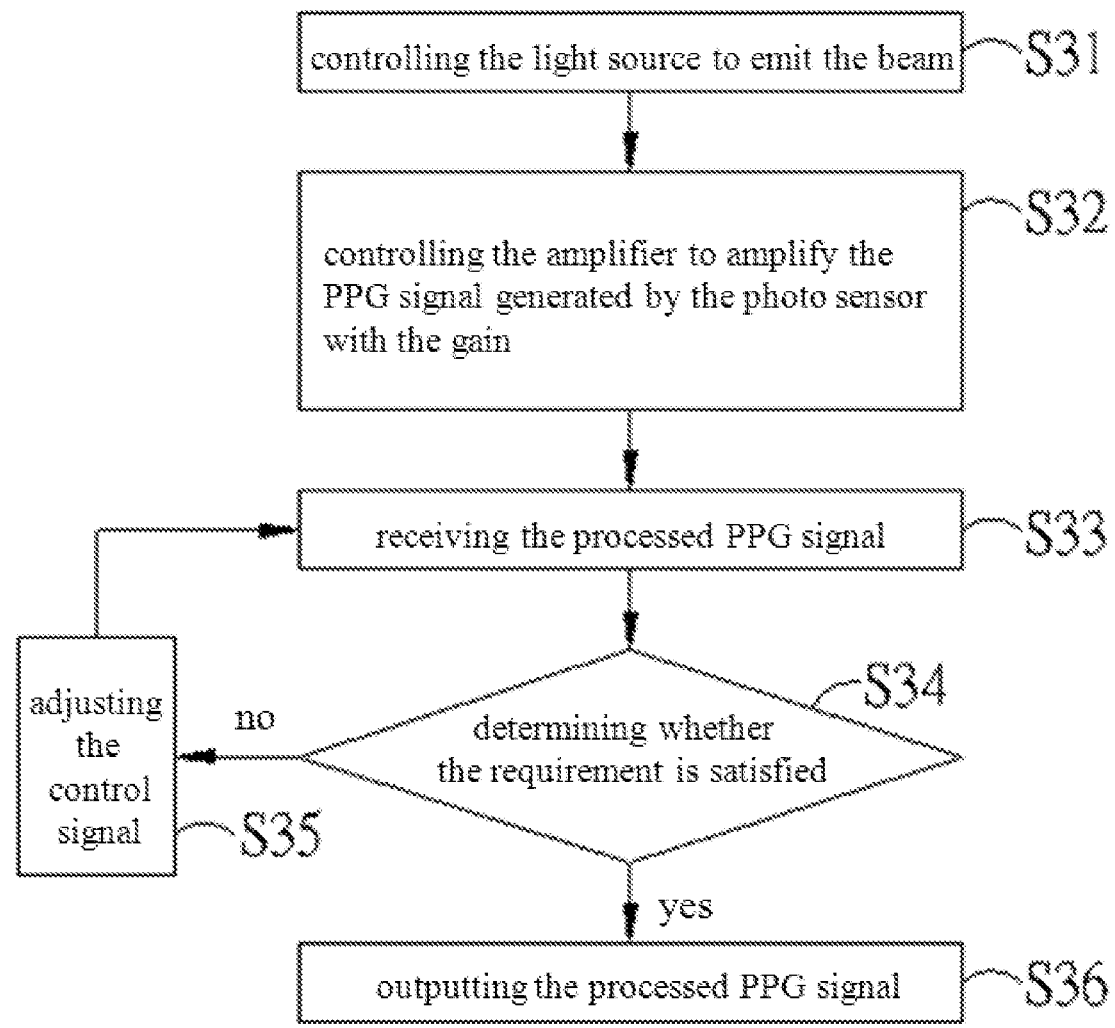
FIG. 3 is flow chart of a control method executed by an adaptive controller in a photoplethysmography sensing system according to another one exemplary embodiment of the present disclosure.

Next, referring to FIG. 3, FIG. 3 is flow chart of a control method executed by an adaptive controller in a photoplethysmography sensing system according to another one exemplary embodiment of the present disclosure. Firstly, at step S31, the adaptive controller controls the light source (such as LED) to emit the beam to the skin surface of the living object, wherein the intensity of the beam is determined according to the amplitude of the driving signal, and the driving signal is determined according to the control signal. In the exemplary embodiment, the intensity of the beam is constant, and the amplitude of the driving signal is constant. Next, the skin surface of the living object reflects the beam emitted by the light source, and the photo sensor receives the reflection beam from the skin surface, and coverts the reflection beam into the PPG signal which is then transmitted to the amplifier. Next, at step S32, the adaptive controller amplifies the PPG signal received and generated from the photo sensor with a gain, wherein the gain is determined according to the control signal, i.e. the value of the gain is determined according to the control signal.

Next, at step S33, the adaptive controller receives the processed PPG signal. Then, at step S34, the adaptive controller determines whether the processed PPG signal satisfies with the requirement. If the processed PPG signal does not satisfy with the processed PPG signal, the adaptive controller adjust the control signal which is used to determine the gain of the amplifier at step S35, and then steps S32 through S34 are executed again. If the processed PPG signal satisfies with the requirement, the adaptive controller outputs the processed PPG signal to the circuit of the next stage at step S36. Steps S32 through S35 are executed repeatedly until the processed PPG signal satisfies with the requirement.

At step S33, it is noted that the processed PPG signal is the PPG signal generated by photo sensor being filtered, peak detected and/or amplified, and the present disclosure is not limited thereto. In addition, whether the processed PPG signal satisfies with the requirement means whether the amplitude or signal stability of the processed PPG signal satisfies with the requirement. For example, whether the amplitude of the PPG signal is larger than or equal to 3 volts is determined. If the amplitude of the PPG signal is larger than or equal to 3 volts, the gain of the amplifier should not be adjust; otherwise, the gain of the amplifier should be adjusted, wherein the gain of the amplifier can be adjusted by varying the control signal. Furthermore, at step S33, the signal quality analysis program is executed in the hardware circuits to determine whether the processed PPG signal satisfies with the requirement. It is noted that, in other exemplary embodiment, the adaptive controller can parameter(s) of control other circuit(s) associated with digital processing to enhance the signal quality of the processed PPG signal. In short, the adaptive controller can optimize the processed PPG signal under the case of low cost.

Figure 4:
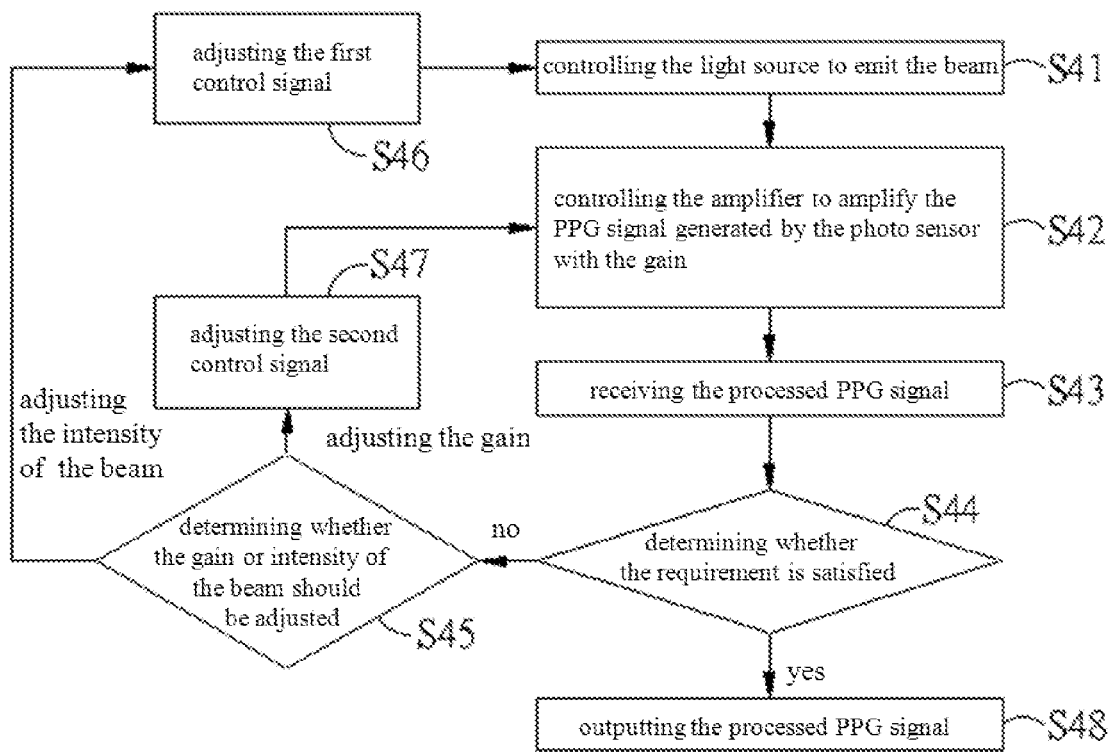
FIG. 4 is flow chart of a control method executed by an adaptive controller in a photoplethysmography sensing system according to another one exemplary embodiment of the present disclosure.

In the exemplary embodiment of FIG. 3, after the gain of the amplifier is further adjusted, though the amplitude of the processed PPG signal can achieve 3 volts, the second peak of the processed PPG signal cannot be found successfully. Thus, the intensity of the beam generated by the light source should be adjusted, so as to find the second peak of the processed PPG signal successfully. Referring to FIG. 4, FIG. 4 is flow chart of a control method executed by an adaptive controller in a photoplethysmography sensing system according to another one exemplary embodiment of the present disclosure. The control method executed in the adaptive controller of FIG. 4 is used to adjust the intensity of the beam generated by the light source and/or the gain of the amplifier. Firstly, at step S41, the adaptive controller controls the light source (such as LED) to emit the beam to the skin surface of the living object, wherein the intensity of the beam is determined according to the amplitude of the driving signal, and the driving signal is determined according to a first control signal generated by the adaptive controller. Next, the skin surface of the living object reflects the beam emitted from the light source, and the photo sensor receives the reflection beam from the skin surface of the living object, and converts the reflection beam into the PPG signal which is then transmitted to the amplifier. Next, at step S42, the adaptive controller controls amplifier to amplify the PPG signal received and generated from photo sensor with the gain, wherein the gain is determined according to a second control signal generated by the adaptive controller, i.e. the value of the gain is determined according the second control signal.

Next, at step S43, the adaptive controller receives the processed PPG signal. Then, the adaptive controller determines whether the processed PPG signal satisfies with the requirement. If the processed PPG signal does not satisfy with the requirement, the adaptive controller determines whether the gain of the amplifier or the intensity of the beam generated by the light source should be adjusted at step S45. If the processed PPG signal satisfies with the requirement, the adaptive controller outputs the processed PPG signal to the circuit of the next stage at step S48. If that the intensity of the beam generated by the light source should be adjusted is determined, step S46 will be executed; if the gain of the amplifier should be adjusted is determined, steps S47 will be executed; if that both of the intensity of the beam generated by the light source and the gain of the amplifier should be adjusted is determined, both of steps S46 and S47 will be executed, but step S47 will be executed after steps S46 and S41 have been executed again, or alternatively, step S42 will be executed after steps S41 have been executed again. At step S46, the adaptive controller adjusts the first control signal which is used to determine the intensity of the beam generated by the light source. At step S47, the adaptive controller adjusts the second control signal which is used to determine the gain of the amplifier. Steps S41 through S45 and at least one of steps S46, S47 are executed repeatedly until the processed PPG signal satisfies with the requirement.

At step S43, it is noted that the processed PPG signal is the PPG signal generated by photo sensor being filtered, peak detected and/or amplified, and the present disclosure is not limited thereto. Furthermore whether the amplitude or signal stability of the processed PPG signal is larger than a predetermined threshold value or falls within a predetermined threshold range is judged, so as to determine whether the processed PPG signal satisfies with the requirement. If the processed PPG signal satisfies with the requirement, both of the intensity of the beam generated by the light source and the gain of the amplifier should not be adjusted; otherwise at least one of the intensity of the beam generated by the light source and the gain of the amplifier should be adjusted. In addition, at step S43, a signal quality analysis program or a smart analysis program is executed by the hardware circuit to determine whether the processed PPG signal satisfies with the requirement, wherein the smart analysis program can have the deep learning program or fuzzy control program associated with the artificial intelligence algorithm, such that the adaptive controller can make the processed PPG signal satisfies with the requirement quickly. It is noted that, in other exemplary embodiment, the adaptive controller can parameter(s) of control other circuit (s) associated with digital processing to enhance the signal quality of the processed PPG signal. In short, the adaptive controller can optimize the processed PPG signal under the case of low cost and low time consumption.

Furthermore, the numbers of the light source and the photo sensor can be larger than one, and the wavelengths corresponding to the light sources and photo sensors can be different. The different wavelengths can be corresponding to the PPG signal conveying different physiology information. By using the smart analysis program, the intensities of the beams generated by the light sources and the gains of the amplifiers can be controlled efficiently, so as to quickly obtain the processed PPG signals which satisfy with the requirements, and acquire the different and precise physiology information. In another one aspect, the physiology information and/or the processed PPG signals can be transmitted to the computing device or cloud server with communication abilities, such that the user can use application program to browse and manage the physiology information. Moreover, the physiology information and/or the processed PPG signals can be compared with physiology information and/or processed PPG signals measured by other medical devices or technologies to establish a calibration model, such that the adaptive controller can quickly obtain the processed PPG signals which satisfy with the requirements.

Figure 5:
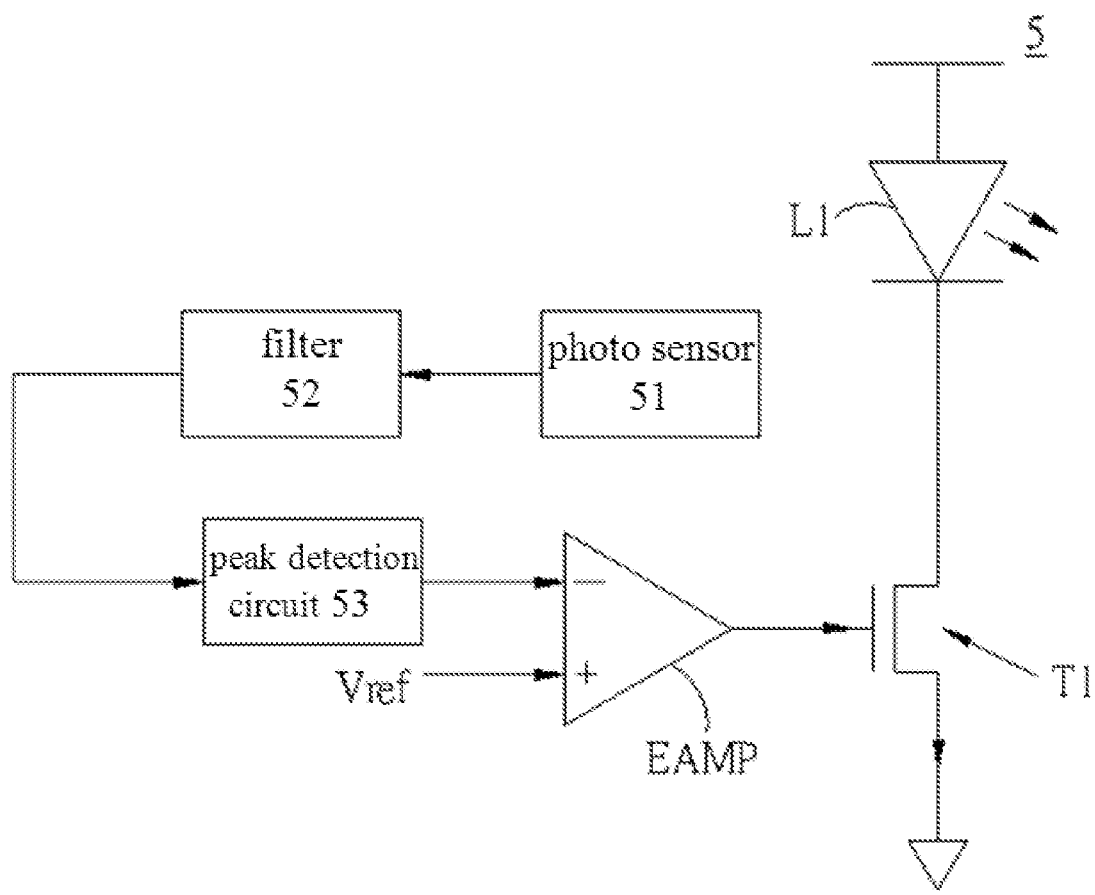
FIG. 5 is a circuit diagram of a photoplethysmography sensing system according to one exemplary embodiment of the present disclosure.

Next, referring to FIG. 5, FIG. 5 is a circuit diagram of a photoplethysmography sensing system according to one exemplary embodiment of the present disclosure. The adaptive controller used in the photoplethysmography sensing system 5 comprises a filter 52, a peak detection circuit 53 and an error amplifier EAMP. The photoplethysmography sensing system 5 comprises the adaptive controller, a light source L1 (for example, LED), a photo sensor 51 and a switch transistor T1. In prior art, a gate of the switch transistor T1 is connected to a constant bias voltage, such that the driving current of the light source L1 is a constant, but in the exemplary embodiment of the present disclosure, the gate of the switch transistor is connected to the adaptive controller to receive the control signal generated by the adaptive controller, so as to adjust the driving current of the light source L1.

Specifically, in the exemplary embodiment of the present disclosure, an input end and an output end of the light source L1 are respectively connected to a bias voltage and a drain of the switch transistor T1. The intensity of the beam emitted by the light source L1 is determined according the driving current. The photo sensor 51 is used to receive the reflection beam, and generate the PPG signal accordingly. An input end of the filter 52 receives the PPG signal, and filters the PPG signal, for example, the noise of low and high frequencies are filtered out. An output end of the filter 52 is electrically connected to an input end of the peak detection circuit 53. The peak detection circuit 53 is used to find the peak of the filtered PPG signal, and output the peak to a negative input end of the error amplifier EAMP through an output end thereof. A positive input end of the error amplifier EAMP receives a reference signal Vref. The error amplifier EAMP compares the peak with reference signal Vref, and outputs control signal generated according to a comparison result to the gate of the switch transistor T1 through an output end thereof. By adjusting the driving current once or server times, the processed PPG signal will finally satisfies with the requirement. In addition, the reference signal Vref is a voltage signal provided by a linear regulator, and the reference signal Vref can be about 1 volt, such that the processed PPG signal is controlled within a range of 0 and 3.3 volts, and the saturation of the processed PPG signal does not occur easily.

Figure 6:
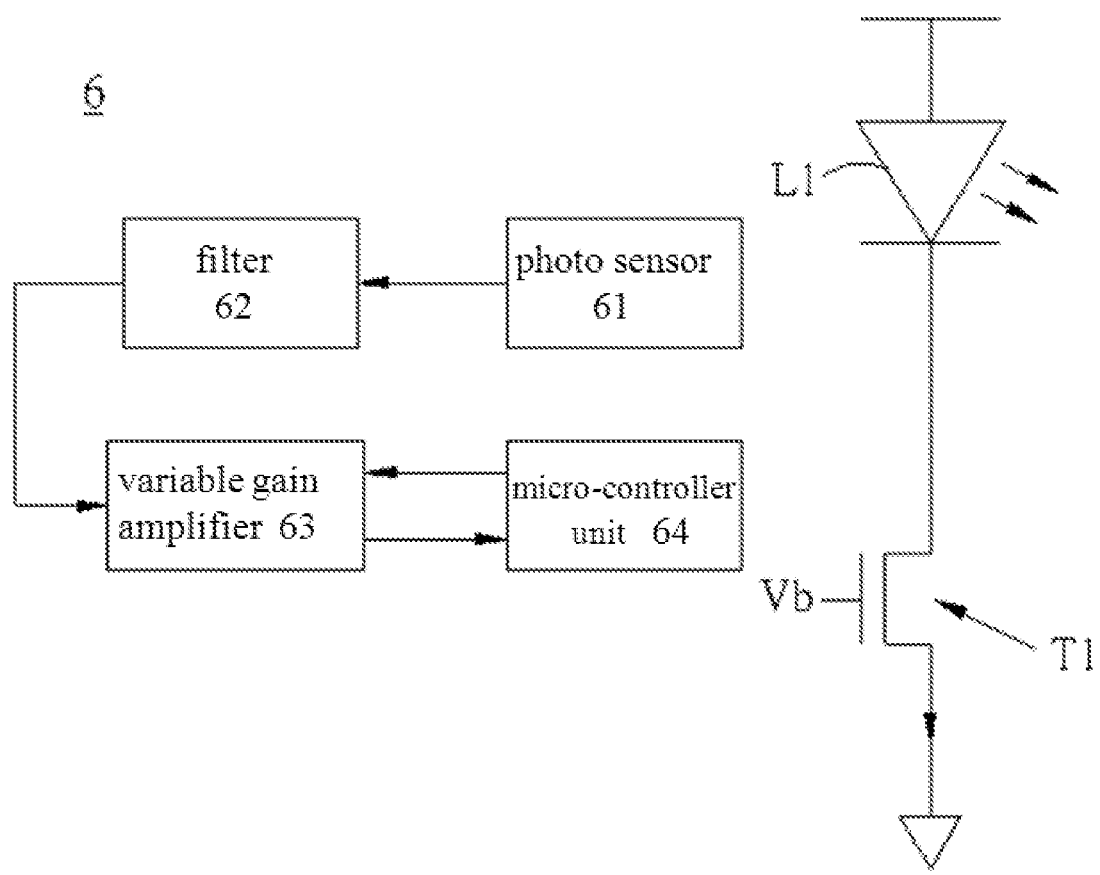
FIG. 6 is a circuit diagram of a photoplethysmography sensing system according to another one exemplary embodiment of the present disclosure.

Referring to FIG. 6, FIG. 6 is a circuit diagram of a photoplethysmography sensing system according to another one exemplary embodiment of the present disclosure. The adaptive controller in the photoplethysmography sensing system 6 comprises a filter 62, a variable gain amplifier 63 and micro-controller unit 64. The photoplethysmography sensing system 6 comprises the adaptive controller, a light source L1 (such as LED), a photo sensor 61 and a switch transistor T1. In the exemplary embodiment, the gate of the switch transistor is connected to the bias voltage Vb, such that the driving current of the light source L1 is the constant.

In the exemplary embodiment of the present disclosure, the input end and the output end of the light source L1 are respectively connected to another one bias voltage and the drain of the switch transistor T1. The intensity of the beam emitted by the light source is determined according to the driving current. The photo sensor 61 is used to receive the reflection beam, and generate the PPG signal accordingly. The input end of the filter 62 receives the PPG signal, and filters the PPG signal, for example, the noise of low and high frequencies are filtered out. The output end of the filter 62 is electrically connected to the input end of the variable gain amplifier 63, and the variable gain amplifier 63 is used to amplify the filtered PPG signal, and the amplified PPG signal is then transmitted to the micro-controller unit 64. The micro-controller unit 64 determines whether the amplified PPG signal is larger than or equal to a predetermined voltage, such as 3 volts. If the micro-controller unit 64 determines that the amplified PPG signal is less than the predetermined voltage, the micro-controller unit 64 generates the control signal to adjust the gain of the variable gain amplifier 63. By contrast, if the amplified PPG signal is larger than or equal to a predetermined voltage, the micro-controller unit 64 will not adjust the gain of the variable gain amplifier 63.

Figure 7:
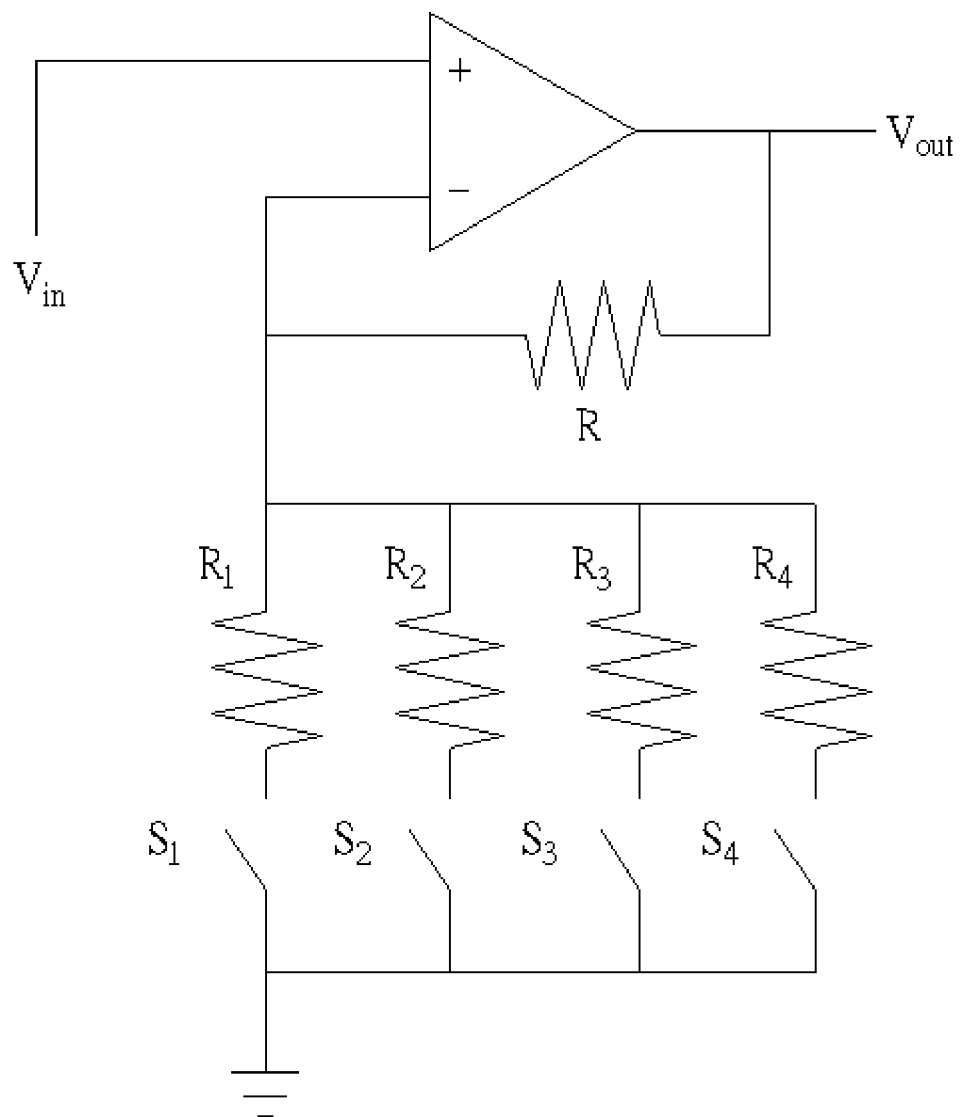
FIG. 7 is a circuit diagram of a variable gain amplifier according to one exemplary embodiment of the present disclosure.

Referring to FIG. 7, FIG. 7 is a circuit diagram of a variable gain amplifier according to one exemplary embodiment of the present disclosure. The variable gain amplifier 63 in FIG. 6 can be implemented by the variable gain amplifier 7 in FIG. 7, and the variable gain amplifier 7 comprises an operation amplifier, resistors R, $R_1$ through $R_4$ and switches $S_1$ through $S_4$. The positive input end of the operation amplifier is used to receive the filtered PPG signal $V_{in}$, the negative input end of operation amplifier is connected to the output end of the operation amplifier through the resistor R, and the output end of the operation amplifier is used to output the amplified PPG signal PPG $V_{out}$. Second ends of the resistors $R_1$ through $R_4$ are connected to the ground voltage through the switches $S_1$ through $S_4$, and first ends of the resistors $R_1$ through $R_4$ are connected to the negative input end of operation amplifier. The switches $S_1$ through $S_4$ are controlled by the control signal transmitted by the micro-controller unit to be turned on or off, so as to adjust the gain of the variable gain amplifier 7.

Figure 8:
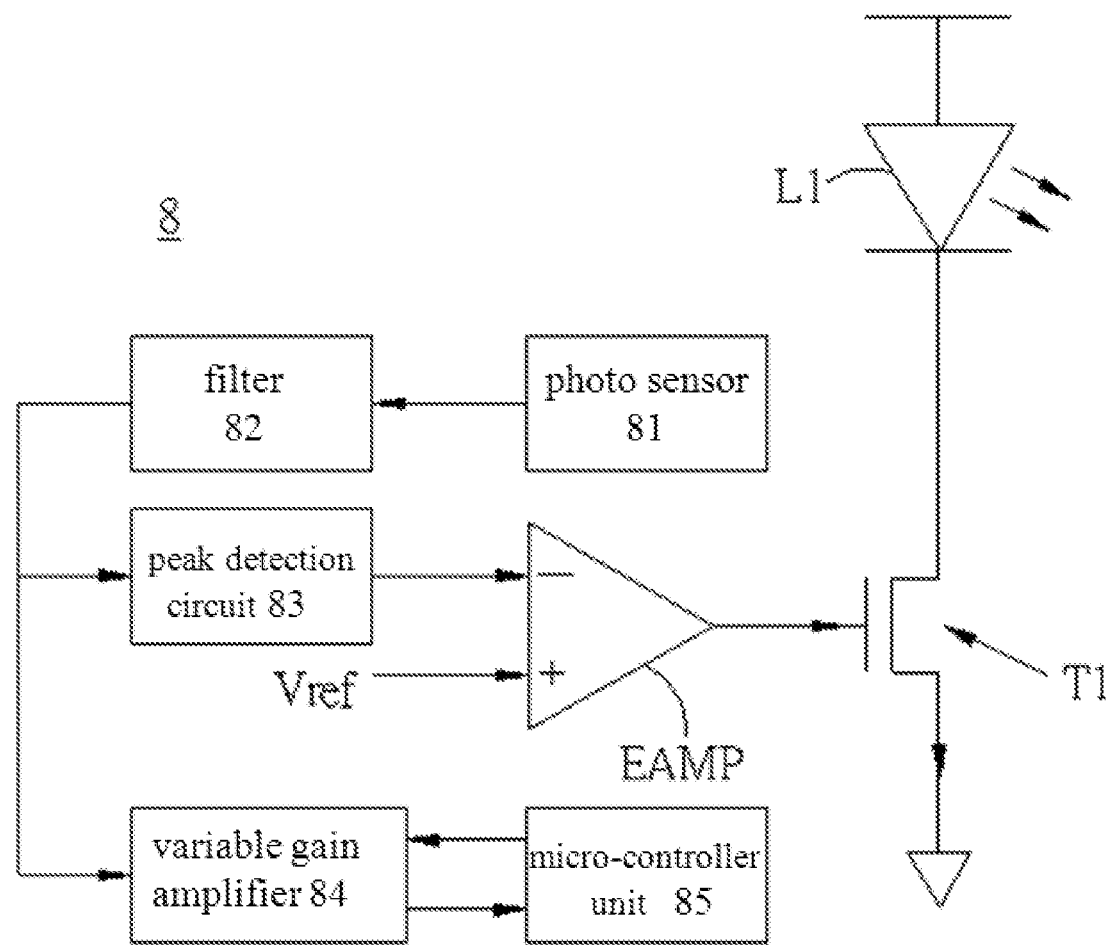
FIG. 8 is a circuit diagram of a photoplethysmography sensing system according to another one exemplary embodiment of the present disclosure.

Referring to FIG. 8, FIG. 8 is a circuit diagram of a photoplethysmography sensing system according to another one exemplary embodiment of the present disclosure. The adaptive controller in the photoplethysmography sensing system 8 comprises a filter 82, a peak detection circuit 83, an error amplifier EAMP, a variable gain amplifier 84 and micro-controller unit 85. The photoplethysmography sensing system 8 comprises the adaptive controller, a light source L1 (such as LED), photo sensor 81 and a switch transistor T1. In prior art, a gate of the switch transistor T1 is connected to a constant bias voltage, such that the driving current of the light source L1 is a constant, but in the exemplary embodiment of the present disclosure, the gate of the switch transistor is connected to the adaptive controller to receive the control signal generated by the adaptive controller, so as to adjust the driving current of the light source L1.

The exemplary embodiment in FIG. 8 in fact is the combination of the exemplary embodiments of FIG. 5 and FIG. 6. Thus, the driving current and the gain of the variable gain amplifier 84 can be adjusted. Functions of the photo sensor 81, the filter 82, the peak detection circuit 83, the error amplifier EAMP, the variable gain amplifier 84, the micro-controller unit 85, the light source L1 and the switch transistors T1 are illustrated in the above exemplary embodiments of FIG. 5 and FIG. 6, and thus the redundant descriptions are omitted.

To sum up, the adaptive controller used in a photoplethysmography sensing system makes the processed PPG signal have high stability, precision and sensitivity. In addition, the implementation cost of the adaptive controller is not high, the adaptive controller can be integrated in the photoplethysmography sensing system easily, and thus the present disclosure has low price advantage and light, thin, short and small properties. Moreover, since the processed PPG signal is optimized without user operation, and thus the photoplethysmography sensing system with the adaptive controller has advantage of simple and convenient operation.

The above-mentioned descriptions represent merely the exemplary embodiment of the present disclosure, without any intention to limit the scope of the present disclosure thereto. Various equivalent changes, alternations or modifications based on the claims of present disclosure are all consequently viewed as being embraced by the scope of the present disclosure.

What is claimed is:

1. An adaptive controller used in a photoplethysmography sensing system, comprising hardware circuits configured to:
   receive a processed photoplethysmography signal (PPG signal);
   determine whether the processed PPG signal satisfies a requirement;
   output the processed PPG signal if the processed PPG signal satisfies the requirement; and
   adjust a gain of an amplifier for amplifying a PPG signal and/or a driving signal of a light source if the processed PPG signal does not satisfy the requirement;
   wherein the hardware circuits comprise:
   a filter used to receive the PPG signal generated by a photo sensor and filter the PPG signal;
   a peak detection circuit used to receive a filtered PPG signal and find a peak of the filtered PPG signal; and
   an error amplifier used to compared the peak with a reference signal and output a control signal to a gate of a switch transistor according to a comparison result, wherein the gate of the switch transistor is connected to an output end of the light source, and thus the driving signal of the light source is adjusted according to the control signal.

2. The adaptive controller used in a photoplethysmography sensing system according to claim 1, wherein a beam generated by the light source is determined by the driving signal.

3. The adaptive controller used in a photoplethysmography sensing system according to claim 1, wherein whether amplitude or signal stability of the processed PPG signal is larger than a predetermined threshold value or falls within a predetermined threshold range is judged, so as to determine whether the processed PPG signal satisfies the requirement.

4. A photoplethysmography sensing system, comprising:
   a light source, used to generate a beam emitting to a skin surface of a living object according to a driving signal;
   a photo sensor, used to receive a reflection beam which the beam is reflected from the skin surface, and generate a PPG signal according to the reflection beam; and
   an adaptive controller, comprising hardware circuits configured to:
   receive a processed PPG signal;
   determine whether the processed PPG signal satisfies a requirement;
   output the processed PPG signal if the processed PPG signal satisfies with the requirement; and
   adjust a gain of an amplifier for amplifying a PPG signal and/or a driving signal of a light source if the processed PPG signal does not satisfy with the requirement;
   wherein the hardware circuits comprise:
   a filter used to receive the PPG signal generated by a photo sensor and filter the PPG signal;
   a peak detection circuit used to receive a filtered PPG signal and find a peak of the filtered PPG signal; and
   an error amplifier used to compared the peak with a reference signal and output a control signal to a gate of a switch transistor according to a comparison result, wherein the gate of the switch transistor is connected to an output end of the light source, and thus the driving signal of the light source is adjusted according to the control signal.

5. The photoplethysmography sensing system according to claim 4, further comprising the amplifier.

6. The photoplethysmography sensing system according to claim 4, wherein whether the amplitude or signal stability of the processed PPG signal is larger than a predetermined threshold value or falls within a predetermined threshold range is judged, so as to determine whether the processed PPG signal satisfies the requirement.

* * * * *